United States Patent [19]

Chang

[11] 4,101,382

[45] Jul. 18, 1978

[54] NOVEL REAGENT AND METHOD FOR THE DETERMINATION OF UREA IN BIOLOGICAL FLUIDS

[76] Inventor: Moon Ki Chang, 1262 Barrington Ave., Apt. 105, Los Angeles, Calif. 90025

[21] Appl. No.: 638,272

[22] Filed: Dec. 5, 1975

Related U.S. Application Data

[62] Division of Ser. No. 519,600, Oct. 31, 1974, Pat. No. 3,950,226.

[51] Int. Cl.$^2$ ............................................ G01N 31/14
[52] U.S. Cl. ........................................ 195/103.5 UR
[58] Field of Search ................. 195/103.5 R, 103.5 U

[56] References Cited

U.S. PATENT DOCUMENTS

| | | | |
|---|---|---|---|
| 3,119,751 | 1/1964 | Chaney | 195/103.5 R |
| 3,527,674 | 9/1970 | Deutsch | 195/103.5 LR |
| 3,542,649 | 11/1970 | Searcy | 195/103.5 R |
| 3,635,681 | 1/1972 | Rogers | 195/103.5 R X |

Primary Examiner—Alvin E. Tanenholtz
Assistant Examiner—C. A. Fan
Attorney, Agent, or Firm—Wills, Green & Mueth

[57] ABSTRACT

The ease and speed of known enzymatic assays of micro-amounts of urea is improved by a novel reagent assay comprising: urease, buffers, and an indicator dye, the improvement wherein a mixed buffer system is present which mitigates against the effects of temperature changes during the assay, and a novel method of determining released ammonia with an indicator dye and spectrophotometer.

6 Claims, 1 Drawing Figure

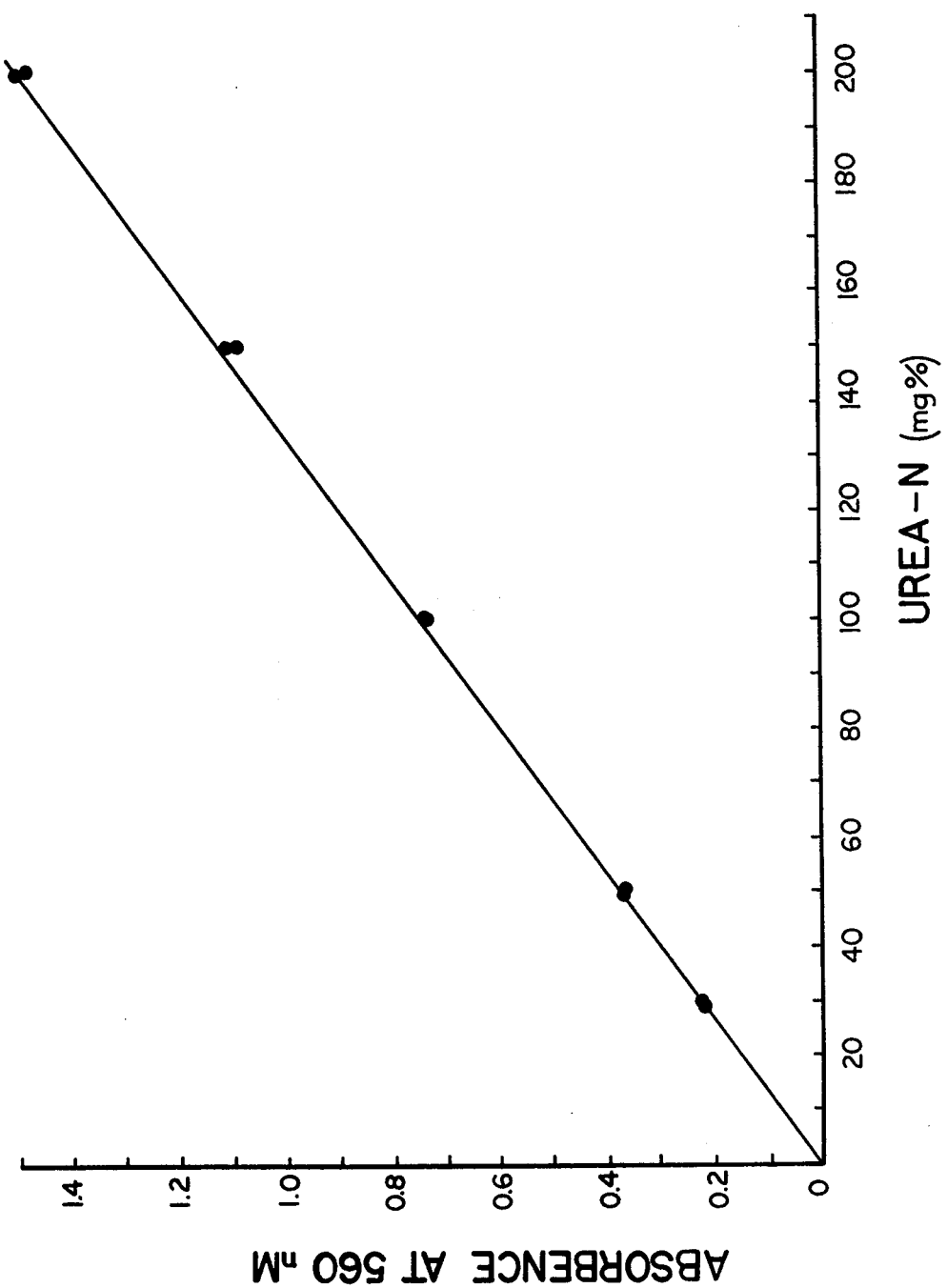

NOVEL REAGENT AND METHOD FOR THE DETERMINATION OF UREA IN BIOLOGICAL FLUIDS

This is a division of application Ser. No. 519,600 filed Oct. 31, 1974, now U.S. Pat. No. 3,950,226, issued Apr. 13, 1976.

BACKGROUND OF THE INVENTION

This invention relates to reagent mixtures useful for detecting and measuring urea.

The determination of urea has been important in the food industry, fertilizer industry, and in clinical chemistry. In clinical chemistry, the determination of urea levels in blood is used routinely as a diagnostic aid in the evaluation of kidney diseases as well as other disease states which are not primarily renal. The method of determining urea in clinical chemistry should ideally be able to measure microgram quantities of urea (due to the low level of urea in serum) with speed, easy, accuracy, and precision. However, the methods of urea analysis normally used in the food and fertilizer industries are far too insensistive for the purposes of clinical chemistry.

The three most widely used methods for the determination of urea in clinical chemistry are the urease-Nessler, urease-Berthelot, and monoximine methods. In the urease-Nessler method, the urea in the unknown specimen is hydrolyzed to carbon dioxide and ammonia. The released ammonia is reacted with mercuric iodide (Nessler's reagent) to give a strong color reaction which is then quantitated colorimetrically. The urease-Berthelot method is similar to the urease-Nessler method except that the released ammonia is reacted with phenol, nitroprusside, and alkaline hypochlorite (Berthelot's reagent) to give the colored reaction. In the monoxime method the urea in the unknown sample is reacted directly with monoxime to give a strong colored complex in the presence of heat and acid.

All of these methods suffer several distinct drawbacks. They include deproteinization, removal of ammonia, nonlinear calibration curves over the clinically useful range, time consuming reaction times and elevated reaction conditions. The enzymatic methods have the advantage of being highly specific due to the specificity of the enzyme urease for urea. They however have the drawbacks of being time consuming, cumbersome to perform, employing toxic reagents, and being highly sensitive to ammonia contamination. The monoxime method has the disadvantage of utilizing toxic chemicals and requiring elevated reaction temperatures up to 100° C to develop the color complex in addition to being less specific than the urease methods.

Another method for the determination of urea involves the use of urease, a buffer, and a pH indicator dye. In such a reaction system, since two moles of $NH_3$ are formed per mole of $CO_2$ upon hydrolysis of urea, the net reaction mixture becomes alkaline. The net increase in alkalinity is determined visually with the aid of a pH indicator dye either (1) titrimetrically or (2) by visual comparison with standard color charts. The former method suffers the disadvantage of being lengthy and cumbersome. The latter method suffers the disadvantage of being at best semiquantitative.

I have discovered a new way of determining urea in biological fluids which overcomes the drawbacks of the other methods just mentioned. That is, it is simpler and faster to perform than the urease methods mentioned above, does not require elevated temperatures for reaction, utilizes harmless chemicals, and is quantitative. The method is conveniently carried out at room temperature and the entire reaction is completed in five minutes.

In the reaction mixture urease catalyzes the reaction:

$$\text{Urea} + 2H_2O \rightarrow 2NH_3 + CO_2$$

Only liberated $NH_3$ is detected in a new unique manner.

SUMMARY OF THE INVENTION

Briefly, the present invention relates to a novel reagent mixture comprising urease, mixed buffers, as more fully hereinafter described, and a pH indicator dye in aqueous solution, or in powder form which is reconstituted with distilled water prior to use. Stabilizing agents may also be present. The urea-containing biological fluid, such as urine, causes an increase in pH proportionate to the amount of urea hydrolyzed to ammonia by the action of urease. The rise in pH causes a proportional change in the absorption of the pH indicator dye, the change of which is quantitated in a suitable spectrophotometer or colorimeter.

Even though the over all system might be understandable to anyone skilled in the art, making the system accurate, precise, reproducible, repeatable, and rugged is far from obvious as evidenced by the fact that such a system has never been used to determine urea in biological fluids.

The parameters which were carefully adjusted to make my system work are the linear proportionality of the change in absorbance (in a photometer) of the indicator dye with the amount of urea contained in a sample to be analyzed and the relative ruggedness (insensitivity) of the system to pertubations of temperature, ionic strength and molecular constituents normally encountered in the performance of urea assays in a routine laboratory.

The linearity of change in absorbance with urea concentration is obtained by properly matching the pKa of the indicator dye with the buffer so that the pKa of the dye approximates at least one of the pKa's of the buffer.

One of the variables most difficult to control in most routine laboratories is small fluctuations in temperature of the reaction mixture. The absorbance of a pH indicator dye will change with a change in temperature for the following reasons:

(1) dilution of dye concentration due to change in volume of reagent fluid with temperature,
(2) decrease in pKa of dye due to increase in temperature,
(3) change in pKa of buffers with change in temperature,
(4) change in ionic strength of reagent system due to change in activity coefficients of ionic species.

In order to minimize the above effects I have found it expedient to:
(1) increase the ionic strength of the reagent with neutral salts such as NaCl, KCl, etc.
(2) to add buffer or buffers which increase in pH with an increase in temperature (+ dpH/dT) such as pyrophosphate and salts and acids thereof.
(3) finally to add buffer or buffers which decrease in pH with an increase in temperature (−dpH/dT) such as substituted amines and substituted phenol buffers.

In general, the mixed buffers and the pH indicator dyes used in the practice of this invention has about the same pKa.

The composition of the solution added to the biological fluid to be tested for urea content is generally as follows:

buffer conc. — 1 to 100 millimoles/liter
dye indicator conc. — 0.05 to 2.0 millimoles/liter
stabilizer conc. — 0 to 100 millimoles/liter
enzyme conc. — 0.1 to 10 international units/ml.

Three ml. of this solution is usually used for from 0.01 to about 1.0 ml. of sera or other biological fluid.

Broadly, it is an object of the present invention to provide a novel reagent mixture.

More particularly, this invention has as one of its objects a procedure for use in the estimation of urea in aqueous solution, including body fluids and tissues.

In yet another aspect, it is an object of this invention to provide an article of manufacture comprising a novel reagent mixture in packaged form.

These and other objects and advantages of this invention will be apparent from the detailed description which follows.

DESCRIPTION OF THE PREFERRED EMBODIMENTS

The particular buffer material that is employed in any particular assay material will be dependent upon the particular assay reaction to be conducted and the other components in the assay material. However, they will be a class of buffers which have a positive dpH/dT. Pyrophosphoric acid ($H_2P_2O_7$) and the positive ion salts thereof such as sodium pyrophosphate, potassium pyrophosphate, and mixtures thereof, may be given as an example. To further prevent the system from being perturbed by temperature the above class of buffers may be fortified with other buffers which have a negative change in pH with a positive change in temperature. Substituted amines and substituted phenols together with their salts may be given by way of example. Examples of such buffers are ethylenediamine, 1,3-diamino-2-hydroxypropane, 1,3-diaminopropane, glycylglycine, tricyne, 5,5-diethylbarbituric acid, triethanolamine, tris(hydroxymethyl) aminomethane, and mixtures thereof. Examples of substituted phenols include cresol, chlorophenol, bromophenol, phenylphenol and methoxy-phenol.

The indicator dye can be any compound which changes its absorption properties with a change in pH, especially in the neutral pH range. By way of example, phenolsulfonphthalein, 2-methyl-3-amino-6-dimethylaminophenazine, o-cresolsulfonphthalein, cyanine, 5,8-quinolinequinone-8-hydroxy-5-quinolyl-5-imide, and dibromothymolsulfonphthalein are useful in the practice of this invention.

The stabilizers have the effect of stabilizing and intensifying the developed color and also prevent large variations of ionic strength in the reagent system upon addition of sample. The stabilizers further prevent the precipitation of proteins in solution upon addition of samples of protein-containing materials such as serum and urine. It has been found the sequestering agents such as ethylene diamine tetraacetic acid (EDTA) and neutral salts such as sodium and potassium chloride were particularly effective in this regard. Any colorimeter or spectrophotometer that transmits light in the neighborhodd of 500–600 nM may be used.

Urea nitrogen may be determined in plasma, serum, urine and other biological fluids in accordance with the method of the present invention without deproteinization or removal of ammonia. While the present invention is particularly applicable to the determination of the urea level in biological fluids, it has general application to the determination of the urea level in any urea-containing fluid. Due to the specificity of urease for urea there is at present no known substance which will result in false urea nitrogen values except for those reagents, which denature the enzyme urease. Since urea may be lost through bacterial action, especially in urine samples, the specimen should be properly preserved by antibacterial agents or refrigerated.

In general, the method is carried out as follows:

1. Make solutions of 10, 20, 50 and 100 mg% urea nitrogen (21.43 mg. 42.87 mg., 107.2 mg. amd 214.3 mg. dry urea, A.R., per 100 ml. distilled water respectively).

2. Run these solutions through the test procedure as hereinafter described.

3. A plot of the results against urea nitrogen yields a straight line in most spectrophotometers up to 200 mg.% urea nitrogen, as shown in the drawing.

4. Without increasing or decreasing the sample volume, it is possible in most spectrophotometers to measure from 5 to 200 mg.% urea nitrogemn with ease. The following examples are presented solely to illustrate the invention, and should not be regarded as limiting in any way. Any size cuvet may be used in the examples below and therefore different sample volumes may be used for different size cuvets. A 3 ml cuvet was chosen for the sake of this example.

EXAMPLE 1

1. A solution consisting of approximately 10 mmol/liter triethanolamine, 10 mmol/liter pyrophosphate, 10 mmol/liter EDTA, 200 mmol/liter sodium chloride and 0.3 mmol/liter phenolsulfonphthalein in distilled water is adjusted to a pH of 6 to 8 with sodium hydroxide or hydrochloric acid. Alternatively a solid mixture containing the above ingredients in appropriate amounts is dissolved in distilled water to give the same final solution.

2. A sample or urease is dissolved in an aliquot of the final solution of step I to give a solution of approximately 100 international units of urease activity per ml at 25° C.

3. Solutions of urea, analytical grade, containing 10, 50 and 100 mg urea nitrogen per 100 ml are made with distilled water.

4. Pipet 2.8 ml. aliquots of final solution of Step 1, Example I into blank cuvet and sample cuvets labeled a, b, c, and blank.

5. Add 0.1 ml. aliquots of 10, 50 and 100 mg. per 100 ml urea solution of Step 3, Example I into cuvets labeled a, b, c, respectively, and mix gently but thoroughly.

6. Record initial absorbance of cuvets a, b, and c against blank cuvet at 560 nM.

7. Add 0.1 ml. aliquots of urease solution of Step 2, Example I, to blank and sample cuvets, mix gently but thorougly and let stand at room temperature for at least 1 minute but not more than 5 hours.

8. Record final absorbance of each sample tube against blank cuvet at 560 nM. Subtract initial absorbance of each sample cuvet from its final absorbance value to obtain change in absorbance.

9. A plot of urea concentration of the samples against the change in absorbance results in a straight line, as illustrated generally in the drawing.

10. The urea concentration of unknown samples of biological fluid may be obtained by subjecting the unknown samples through the Steps 1 through 8 stated above and comparing the results obtained against solutions with known urea concentration.

It is customary in most laboratories to express urea as urea nitrogen. This came about through the desire to compare the quantity of nitrogen in urea with that of other components included in the non-protein category. Since the molecular weight of urea is 60 and it contains 2 nitrogen atoms with a combined weight of 28, a urea nitrogen value can be converted to a urea value by multiplying by 60/28 or 2.14.

Calculation:
1. Subtract initial absorbance from final absorbance to obtain A of sample and 50 mg% urea nitrogen standard.
2. mg% urea nitrogen = 50 × (Δ A of sample/Δ A of standard)
3. mg% urea = mg% urea nitrogen × 2.14

Sample calculation:

| 50 mg % urea nitrogen standard - | Initial absorbance | = −0.04 |
|---|---|---|
|  | Final absorbance | = 0.46 |
|  | ΔA | = 0.50 |
| Sample - | Initial absorbance | = 0.10 |
|  | Final absorbance | = 0.20 |
|  | ΔA | = 0.10 |

$$BUN = 50 \times \frac{10}{50} = 10 \text{ mg. }\%$$

Normal Range (1):
Plasma or serum — 7 to 18 mg% urea nitrogen (15 to 38 mg% urea)
Urine — 12 to 20 gm. urea nitrogen/24 hr. (12 to 43 gm. urea/24 hr).

EXAMPLE II

1. One part of the final solution in Step 2, Example I is mixed with 29 parts of the final solution in Step 1, Example I.
2. Pipet 2.9 ml of solution of Step 3 into cuvets labeled a,b,c, and blank.
3. Add 0.1 ml. aliquots of the 10, 50, and 100 mg. urea nitrogen per 100 ml. solutions of Step 3, Example I, into sample cuvets labeled a, b, and c, respectively, and mix gently but thoroughly. The solutions are permitted to stand at room temperature (above 20° C) for at least 1 minute but not more than about 5 hours.
4. Record final absorbance of cuvets labeled a, b, and c against blank cuvet.
5. A plot of change in absorbance of each sample versus the urea concentration of the samples will result in a straight line, as illustrated generally in the drawing.
6. The concentration of the urea in an unknown sample may be obtained by putting a sample of biological fluid of unknown urea content through steps 1 to 4 stated above instead of the known urea solutions, and comparing the results obtained with the results of the solution containing a known amount of urea. This is done simply by measuring the absorbance of the unknown and reading the urea concentration corresponding to the measured absorbance on the linear plot.

EXAMPLE III

Alternately, a solid mixture containing appropriate amounts of buffers, indicator dyes, stabilizers, and urease is dissolved in distilled water to give the same final solution mentioned in Step 1 of Example II. Otherwise, the procedure is carried out as described in Example II.

EXAMPLE IV

1. Pipet 3 ml aliquot of final solution of step 1, Example I into blank cuvet and 2.9 ml of final solution of Step 1, Example 1 into sample cuvet.
2. Add 0.1 ml of final solution of Step 2, Example I in to sample cuvet. Alternatively add 3.0 ml of the final solution of Step 1, Example 2 into sample cuvet and 3 ml of the final solution of Step 1, Example I to blank cuvet.
3. Add 0.1 ml aliquots of 10 mg per 100 ml urea nitrogen standard of step 3, Example I to both blank and sample cuvets and mix gently but thoroughly. The solutions are permitted to stand at room temperature for at least 1 minute but not more than 5 hours.
4. Record absorbance of sample cuvet against blank cuvet.
5. Repeat Steps 1–4 of above with 50 mg and 100 mg per 100 ml urea nitrogen standards.
6. A plot of urea concentration of the samples against the change in absorbance results in a straight line.
7. The urea concentration of unknown samples of biological fluid may be obtained by subjecting the unknown samples through the steps 1 through 4 above and comparing the results obtained against solutions with known urea concentration.

EXAMPLE V

1. Pipet 3 ml aliquots of final solution of Step 1, Example I into blank and sample cuvets.
2. Add 10 IU of dry urease or an appropriate amount of a concentrator stabilized urease solution as urease in 50% glycerol to sample cuvet and dissolve by gently stirring.

Steps 3 to 7 are identical to Example IV.

EXAMPLE VI

1. Alternatively, a solid mixture containing appropriate amounts of buffers, indicator dyes, and stabilizers is dissolved in distilled water to give the same final solution mentioned in Step 1 of Example IV.
2. Alternatively, solid mixtures containing appropriate amounts of buffers, indicator dyes, stabilizers and urease is dissolved in distilled water to give the same final solution mentioned in step 2 of Example IV Steps 3 to 7 are identical to Example IV.

EXAMPLE VII

1. Alternatively a solid mixture containing appropriate amounts of buffers, indicator dyes, and stabilizers is dissolved in distilled water to give the same final solution mentioned in step 1 of Example V. Otherwise, the procedure is carried out as described in Example V.

In every case where urease has been specified to be in solution form, it can also be used in powder form or in the form of a highly concentrated solution.

Having fully described the invention, it is intended that it be limited only by the lawful scope of the appended claims.

I claim:

1. The method of determining the urea level in urea-containing fluids which comprises:
    1. adding in one step a specimen of said fluid to an aqueous solution of a buffer, a pH indicator dye, a stabilizer of the solution, and measuring the absorbence of the resulting solution,
    2. adding urease to the above resultant solution and measuring the absorbence of the final solution after the hydrolysis of urea by urease has gone to completion, and
    3. calculating the amount of urea in the unknown sample by comparing the change in absorbance of the specimen with the change in absorbance obtained from subjecting specimens containing known amounts of urea to steps 1 and 2.

2. The method of claim 1 wherein said aqueous solution contains from 1 to 100 millimoles per liter of buffer, from 0.05 to 2.0 millimoles per liter of pH indicator dye, from 0 to 100 millimoles per liter of stabilizer, and from 0.1 to 10 international units per milliter of urease.

3. The method of claim 1 wherein the absorbence of the specimens are measured before and again after the urease has liberated the ammonia, the change in absorption of each specimen is plotted against the urea content of the specimens of known urea content to form a graph, and reading the urea content of said specimen of urea-containing fluid from said graph.

4. The method of determining the urea levels in urea-containing fluids which comprises:
    1. adding in one step a specimen of said fluid to an aqueous solution of a buffer, a pH indicator dye, a stabilizer therefor, and urease,
    2. measuring the absorbence of the resulting solution following the total conversion of the urea in the urea-containing fluid to ammonia by the urease,
    3. calculating the amount of urea in the known sample by comparing the absorbtion of the said specimen with the absorbtion measured on specimens containing known amounts of urea which have been subjected to steps 1 and 2.

5. The method of claim 4 wherein said aqueous solution contains from 1 to 100 millimoles per liter of buffer, from 0.05 to 2.0 millimoles per liter of pH indicator dye, from 0 to 100 millimoles per liter of stabilizer, and from 0.1 to 10 international units per milliliter of urease.

6. The method of claim 4 wherein the absorbence of the specimens are measured before and again after the urease has liberated the ammonia, the change in absorbtion of each specimen is plotted against the urea content of the specimens of known urea content to form a graph, and reading the urea content of said specimen of urea-containing fluid from said graph.

* * * * *